Figure 1A:
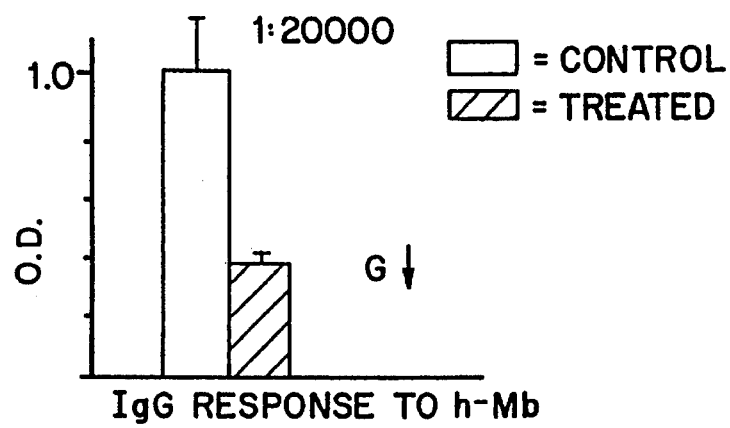
Figure 1B:
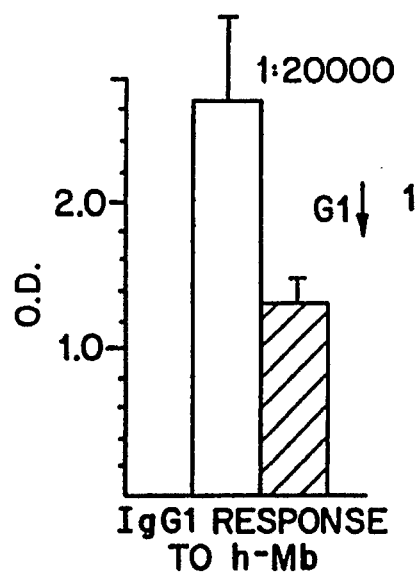
Figure 1C:
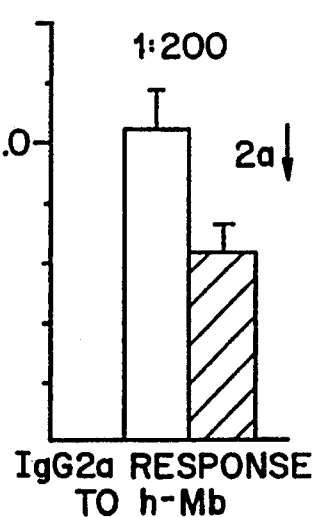
Figure 1D:
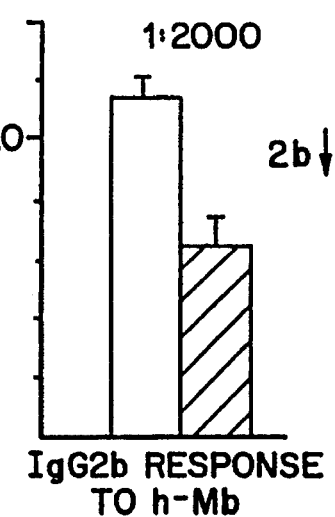
Figure 2:
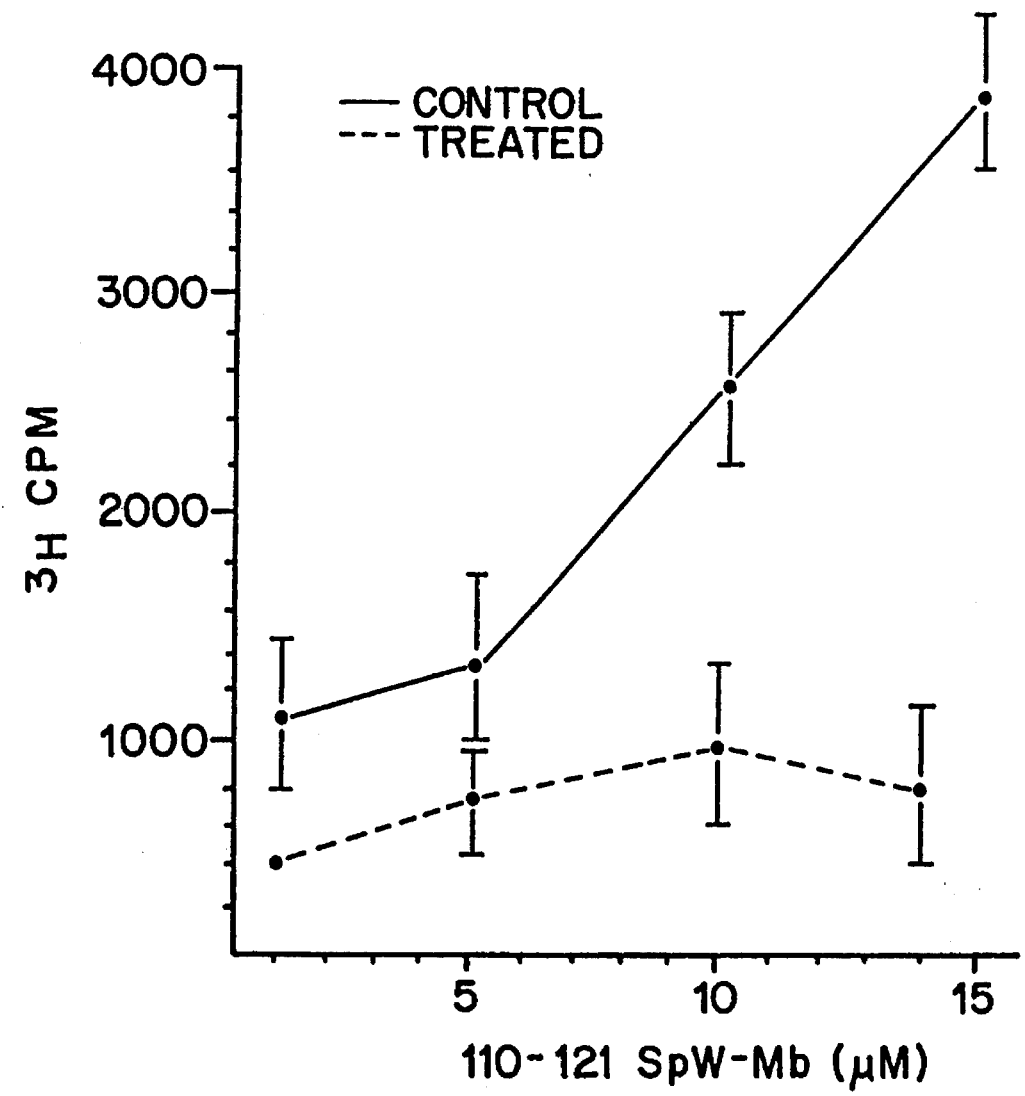

United States Patent [19]
Melmon et al.

[11] Patent Number: 5,556,872
[45] Date of Patent: Sep. 17, 1996

[54] HISTAMINE DERIVATIVES USEFUL AS IMMUNOMODULATORS

[75] Inventors: Kenneth L. Melmon, Woodside; Parisa Khosropour, Palo Alto; Murray Goodman, La Jolla, all of Calif.

[73] Assignee: The Board of Trustees of the Leland Stanford Junior University, Stanford, Calif.

[21] Appl. No.: 483,947

[22] Filed: Jun. 7, 1995

Related U.S. Application Data

[63] Continuation of Ser. No. 146,837, Nov. 12, 1993, abandoned, which is a continuation of Ser. No. 826,578, Jan. 27, 1992, abandoned.

[51] Int. Cl.$^6$ .................... A61K 31/415; C07D 233/64
[52] U.S. Cl. ........................................ 514/400; 548/341.5
[58] Field of Search ......................... 514/400; 548/341.5

[56] References Cited

U.S. PATENT DOCUMENTS

| | | |
|---|---|---|
| 2,988,478 | 6/1961 | Gordon . |
| 4,333,946 | 6/1982 | Durant et al. . |
| 4,340,596 | 7/1982 | Furukawa et al. . |
| 4,532,331 | 7/1985 | Frazee et al. . |
| 4,687,873 | 8/1987 | Goodman et al. . |
| 4,837,305 | 6/1989 | Goodman et al. . |
| 4,996,221 | 2/1991 | Melmon et al. ................. 514/399 |

FOREIGN PATENT DOCUMENTS

| | | |
|---|---|---|
| 0010418 | 4/1980 | European Pat. Off. . |
| 0208953 | 1/1987 | European Pat. Off. . |
| 2454795 | 5/1975 | Germany . |
| 8602620 | 10/1986 | South Africa . |
| 889706 | 2/1962 | United Kingdom . |

OTHER PUBLICATIONS

Rudinger, J. "Characteristics of the amino acids as components of a peptide hormone sequence" in *Peptide Hormones* Parsons, J. A. ed., Univ. Park Press (1976) pp. 1–7.

Khan, et al. "The Effects of Autacoids on Cloned Murine Lymphoid Cells: Modulation of IL–2 Secretion and the Activity of Natural Suppressor Cells" J. Immunol. 134:4100–4106 (1985).

Khan, et al. "The Effects of Derivatives of Histamine on Natural Suppressor Cells" J. Immunol. 137:308–314 (1986).

Qiu, et al. "Effects of Histamine–Trifluoromethyl–Toluidide Derivative (HTMT) on Intracellular Calcium in Human Lymphocytes", J. Pharmacology and Experimental Therapeutics 253:1245–1251 (1990).

Melmon, K. L. and Khan, M. M. "Considering Receptor Non–Specificity as a Factor for Developing Effect, Tissue, and Receptor Specific Agents" in *Enzymes as Targets for Drug Design*, pp. 45–57, Academic Press (1990).

Khan et al. Proc West Phamacol. Soc 30 (1987) pp. 383–387.

Khan et al. J. Med. Chem 30 Noll, (1987) pp. 2115–2120.

Khan, et al., "Congener Derivatives and Conjugates of Histamine: Synthesis and Tissue . . . ", *J. Med. Chem.*, 1987, vol. 30, pp. 2115–2120.

Khan, et al., "Receptor and Tissue Specific Derivatives of Histamine: Novel Imune Modulators", Proc. West. Pharmacol. Soc., vol. 30, 1987, vol. 383–387.

*Primary Examiner*—Johann Richter
*Assistant Examiner*—Michael G. Ambrose
*Attorney, Agent, or Firm*—Cooley Godward Castro Huddleson & Tatum

[57] ABSTRACT

The present invention provides histamine derivatives and methods for using histamine derivatives as immunomodulators and in immunotherapeutics. More specifically the present invention provides methods for inhibiting at least a portion of an an antigen specific antibody response and/or a portion of a T-cell proliferative response by the immune system of a mammal comprising administering to said mammal an effective amount of a composition comprising at least one histamine derivative having binding specificity for at least one histamine receptor.

9 Claims, 3 Drawing Sheets

Experiment #24: Study of Subclassification and IgG Response

IMMUNIZATION SCHEDULE:

| | |
|---|---|
| Treated w/0.5 mg 265 - Compound 1 | Day -1 |
| Immunized w/100 μg h-Mb | Day 0 |
| Treated w/0.5 mg 265   Compound 1 | Day +2 |
| Treated w/0.5 mg 265   Compound 1 | Day +37 |
| Immunized w/100 μg h-Mb | Day +38 |
| Treated w/0.5 mg 265   Compound 1 | Day +40 |

*IgG2b, IgG3 levels were too low to detect at this dilution.

HISTAMINE DERIVATIVES USEFUL AS IMMUNOMODULATORS

This invention was made with Government support under contract HL26403 and AI23463 awarded by the National Institute of Health. The Government has certain rights in this invention.

CROSS REFERENCE TO RELATED APPLICATIONS

This application is a continuation of U.S. application Ser. No. 08/146,837, filed Nov. 12, 1993, now abandoned, which is a continuation of Ser. No. 07/826,578, filed Jan. 27, 1992, now abandoned.

FIELD OF THE INVENTION

The invention relates generally to histamine derivatives and methods for modulating the immune system of mammals and more particularly, to methods of modulating the immune system using compositions comprising histamine derivatives.

BACKGROUND OF THE INVENTION

With the increased level of understanding concerning the immune response process in mammals, there is a growing awareness that certain molecules are generally nonspecific as to their effects on single cell types in a mixture of cells. A critical need exists for agonists that are effect or cell specific.

Histamine is a small molecule that has been shown to have a significant role in the immune response process in mammals. However, its ubiquitous effects on many cells that have receptors for histamine limits its possible immunotherapeutic use. Histamine derivatives that are tissue-directed or effect-specific would significantly aid in determining the role of histamine in immune modulation and produce valuable immunotherapeutics.

Histamine can substantially modulate models of immune responses in mammals, particularly models of delayed hypersensitivity and T and B cell functions. Histamine is synthesized during different phases of response to antigen and is able directly or indirectly to effect further responses to antigen. It is possible that the concentration of histamine in tissue during inflammation and immune response can modify the function of a number of lymphoid cells. Although these effects may be substantial, the direct effect on single cell types in a mixture of cells cannot be determined unless the agonists are effect or cell specific. Ubiquitous effects of agonists on all cells that have receptors for histamine would limit any immunotherapeutic use of histamine. See Khan, et al., Clin. Immunol. Rev. (1985), Melmon, et al. Am. J. Med. (1981) 71:100, and Roclin et al., Cell Immunol. (1978) 37:162.

Histamine is an autacoid as are catecholamines, prostaglandins and some peptides, e.g., bradykinin and probably lymphokines. Autacoids differ from hormones in that they are made at their local sites of action and they can be made in a variety of tissues. Autacoids play an important role in mediating inflammation. During inflammation, certain events may occur which include: protein denaturation, lowering of local pH, release of "new peptides" and lysosomal enzymes, and the like. Such events create a setting in which the immune system should not overreact to the new products. Yet, despite the ability of inflammation to generate likely immunogens, the inflammatory process usually is not accompanied or followed by grossly abnormal immune responses. Autacoids appear to somehow modulate this response.

Autacoids affect natural suppressor cells, T cell subsets and B cells during various stages of immunity. Receptors for autacoids are non-randomly distributed (in number and affinity for agonist) on cells that carry out immune functions. Precursor B cells do not appear to have histamine and catecholamine receptors, while B cells committed to produce antibodies do. T suppressor ($T_s$) cells modulate the CAMP responses of T helper ($T_h$) and T cytolitic ($T_c$) cells to histamine. Mitogens alter responsiveness of these cells to histamine. In some cells biologic response is inhibitory (e.g. reduced release of antibody from B cells: inhibition of lymphokine release or lysis of target cells by T effector cells and inhibition of release of histamine from mast cells); in other the response enhances immune function (e.g. enhanced suppression by natural suppressor and $T_s$ cells or T helper ($T_h$) cell proliferation). The autacoids seem to be enhancing selected early events in immune response (e.g. enhanced suppressor function) while inhibiting later phases of phenotypic manifestations (e.g. release of lymphokines or antibodies) of immunity.

The appearance of naturally occurring suppressor cells in the spleens of neonatal or irradiated mice may have a key role in induction of immune tolerance. See Strober et al., Ann. Rev. Immunol. (1984) 2:219; Hertel-Wulff et al., J. Immunol. (1984) 133:2791; Okada et al., J. Expt. Med. (1982) 156:522; and Okada et al., J. Immunol. (1982) 129:1892. These cells are related to NK cells in terms of their surface phenotype but differ in function. The natural suppressor cells appear briefly during the early maturation of lymphold tissue but can be induced in adults by total lymphold irradiation. The cells have the unique feature of inhibiting the antigen-specific cytolytic arm of alloractive immune response but leave the antigen-specific cytolytic arm intact. In this way, alloreactions in the regulatory milieu of natural suppressor (NS) cells generate large numbers of antigen-specific suppressor cells that in turn maintain tolerance in vivo. Thus, the natural suppressor cells may play an important role in preventing the development of host versus graft and graft versus host diseases in allogenic bone marrow chimeras, and in immune tolerance in the neonatal and total lymphold irradiated (TLI) mice.

Histamine activates human $T_s$ cells and enhances the suppressive ability of murine NS cells in vitro. See Khan et al., J. Immunol. (1985) 134:4100 and Sansoni et al., J. Clin. Invest. (1985) 75:650. After pretreatment of both human $T_s$ cells (leu2., 9.3) with histamine, both phytohemagglutinin-induced $T_h$ proliferation and pokeweed mitogen-induced B cell differentiation were inhibited. The effects were mediated via $H_2$ receptors. Natural suppressor cells can be propagated and cloned in long-term tissue culture and cause nonspecific suppression in both in vitro and in vivo models of mixed leukocyte reactions.

Therefore, methods using histamine derivatives that have little or no systemic effects in immune modulation and immunotherapeutics would be advantageous.

SUMMARY OF THE INVENTION

The present invention provides histamine derivatives preferably having the following formula:

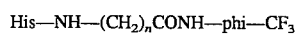

(Formula 1)

where n=2–10, more preferably wherein n=3–6, and most preferably wherein n=5; and

His—NH—CHCH3—(CH2)$_n$CONH—phi—CF$_3$ (Formula 2)

where n=2–10, preferably 3–6, more preferably 4.

In Formula 1 and Formula 2, phi is phenylene, particularly para-phenylene.

The invention further provides methods for inhibiting at least a portion of an antigen specific antibody response and/or a portion of a T cell proliferative response by the immune system of a mammal comprising administering to the mammal an effective amount of a composition comprising at least one histamine derivative having binding specificity for at least one histamine receptor e.g. H1, H2, H3, or Hx and a pharmaceutically acceptable carrier or diluent. The invention also provides methods of treating T cell mediated diseases and graft rejection in an individual by administering to the individual a therapeutically effective amount of a composition comprising at least one histamine derivative having binding specificity for at least one histamine receptor and a pharmaceutically acceptable carrier or diluent.

BRIEF DESCRIPTION OF THE DRAWINGS

FIGS. 1(*a–d*) show the results of an immunization protocol using an embodiment of the invention.

FIG. 2 shows the results of a T-cell proliferation study.

FIGS. 3(*a–d*) show responses to Compound 1.

DETAILED DESCRIPTION OF THE INVENTION

The present invention provides histamine derivatives (also known as a histamine congeners) having the formulas:

His—NH—$(CH_2)_n$CONH—phi—$CF_3$ (Formula 1)

where n=2–10, preferably 3–6, most preferably 5. and

His—NH—CHCH3—$(CH2)_n$CONH—phi—$CF_3$ (Formula 2)

where n=2–10, preferably 3–6, more preferably 4.

Histamine derivatives of particular interest have the following formulas:

His—NH—$(CH_2)_5$CONH—phi—$CF_3$ (Compound 3)

His—NH—$CHCH_3$—$(CH2)_3$—CONH—phi—$CF_3$ (Compound 2)

His—NH—CHCH3—$(CH2)_4$CONH—phi—$CF_3$ (Compound 1)

The histamine derivatives of the inventions may be synthesized by various methods according to procedures well known in the art. A discussion of the synthesis of the above-described histamine derivatives can be found in U.S. Pat. No. 4,996,221, incorporated herein by reference.

The histamine derivatives may be purified by conventional purification techniques, such as crystalization, or by chromatographic techniques, such as column chromatography, high performance liquid chromatography, preparative thin-layer chromatography, or the like.

It is understood that the subject invention includes derivatives of histamine wherein histamine is connected to a linking group to an amino acid of poly(amino acid) molecule thereby defining a conjugate. The histamine derivative may be linked to a carrier such as polypeptides, proteins, glycoproteins or derivatives thereof (all included within the name poly(amino acid).

The conjugates may serve a variety of functions, changing the physiological character of the histamine derivative, acting as immunogens, providing for cell specific binding and the like. Depending on the purpose of the conjugate, the nature of the histamine derivative may be modified to lesser or greater degrees by adding additional functionalities, substituting groups or the like. Particularly for the production of antibodies from immunogens, a group may be substituted for another group, e.g. methyl or trifluoromethyl with carboxyl. Also, in the case of immunogens, substitution at histamine or intermediate the ends of histamine derivative may be desirable.

The conjugates may be bonded through a wide variety of functionalites to form amide, methyleneamine, thioether, disulfide, sulfonamide, azo, amidine, etc. The particular functionality chosen will depend upon the purpose of the conjugate, ease of synthesis, stability of the linking functionality, affect of the linking group on the physical chemical like.

The number of histamine derivatives per carrier may be one, or any number greater than one. The number of histamine derivatives per carrier molecule is dependent upon the number of appropriate functional groups in the carrier and the stoichiometry used during the coupling reaction.

Synthesis routes are well known in the art. One method would involve the preparation of appropriate histamine derivatives where the extended amine side chain or other location on histamine has a suitable functional group. One or more functionalized histamine derivatives are then, in turn, coupled to appropriate side chains of the carrier. Alternatively, a method of synthesis may involve the initial modification of the carrier by coupling the derivative group moiety containing a further functional group reactive with histamine directly to the carrier side chain. The resulting carrier derivative is then coupled directly to the histamine, for example, by a reductive amination reaction to produce the conjugate.

A number of specific physiologic and immunologic factors lead to non-random expression of histamine receptors and their subtypes on various cells responsible for the immune response. Table 1 summarizes the histamine receptor activity of various derivatives of histamine:

TABLE 1

Dominant Interactions of Congeners with Histamine Receptors on Human Lymphocytes, Monocytes and Neutrophils

| Compound # | $H_1$ | $H_2$ | $H_3$ | $H_x$ |
|---|---|---|---|---|
| 1 | ++ | ++ | Anti$H_x$ | +++ |
| 2 | +++ | − | NT | + |
| 3 | − | +++ | NT | ++ |
| Histamine | + | + | + | Anti$H_x$ |

Compound 3 has been shown to have H2 receptor activity but not H1 receptor activity, and further has some Hx activity. As referred to herein, a compound which has receptor activity can bind to a specific receptor. It is believed that compounds having H1 receptor activity enhance the suppressive capacity of the natural suppressor cells via H1 receptor mediated mechanisms. It is believed that compounds having H2 receptor activity effect immune cell modulation by stimulating intracellular accumulations of cAMP.

Hx receptors are believed to be found only in human monocytes, neutrophils, and HL-60 cells that have been transformed. The Hx receptor system is believed to play a role in mediating certain immune responses such as suppressing IL-4 secretion from T helper cells, inhibiting natural T-killer cell activity, enhancing suppression caused by natural suppressor cells and increasing the calcium flux in HL-60 cells and human peripheral blood lymphocytes (PBL). Therefore, compounds having Hx receptor activity are believed to have an effect on these processes.

Although different autacoids certainly share a number of molecular mechanisms of effect and do produce similar effects of immunosuppression, the fine specificity of histamine receptors and their interactions with the congeners provide the potential for orchestrating the use of the likely complementary effects produced by combinations of congeners. In order to achieve a desired effect, it may be beneficial to provide a composition comprising two or more histamine derivatives. Preferably such a composition comprising two or more compounds is selected from the groups consisting of:

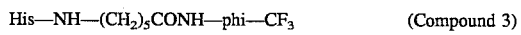
His—NH—(CH$_2$)$_5$CONH—phi—CF$_3$   (Compound 3)

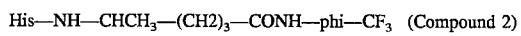
His—NH—CHCH$_3$—(CH2)$_3$—CONH—phi—CF$_3$   (Compound 2)

His—NH—CHCH$_3$—(CH2)$_4$CONH—phi—CF$_3$   (Compound 1)

In one embodiment of the invention, the histamine derivatives of Formulas 1 and/or 2 are useful in methods of inhibiting at least a portion of an antigen specific antibody response by the immune system of a mammal. In particular, administration of an effective amount of at least one histamine derivative having binding specificity for at least one histamine receptor inhibits the production of IgG antibodies while it appears that the production of IgM antibodies are not inhibited. Administration of at least one histamine derivative of Formulas 1 and/or 2 results in inhibition of an antigen specific antibody response by the immune system of a mammal of at least about 60% inhibition of the production of total IgG antibodies, of which at least 40% of the production of IgG1 antibodies are inhibited, at least 40% of the production of IgG2a antibodies are inhibited and at least 40% of the production of IgG2b antibodies are inhibited. In particular, the specific histamine derivatives, Compound 3 and/or Compound 1, will be of interest in inhibiting these antigen specific antibody responses.

Furthermore, at least one histamine derivative of Formula 1 is useful in inhibiting at least a portion of an antigen specific T cell proliferative response by the immune systems of a mammal. In particular, administration of an effective amount of such a histamine derivative inhibits T cell proliferation by at least 60% and preferably by at least 80%. The inhibition is dependent on the dose of the histamine derivative, can endure for extended periods of time, and can be prolonged by repeated dosing of the histamine derivative.

Another embodiment of the present invention provides methods of treating T cell mediated diseases or a method of treating graft rejection in an individual comprising administering to the individual a therapeutically effective amount of a therapeutic composition comprising at least one histamine derivative of Formulas 1 and/or 2 along with a pharmaceutically acceptable carrier or diluent. T cell mediated diseases which can be treated include but are not limited to diabetes, T cell leukemia, endotoxin induced food poisoning and mycosis fungoides. In particular, the specific histamine derivatives, Compound 3 and/or Compound 1, will be of interest in treating T cell mediated diseases or treating graft rejection in an individual.

The manner in which a composition comprising at least one histamine derivative of Formulas 1 and/or 2 is administered to a mammal varies widely in accordance with methods well known in the art. The composition is preferably administered with a physiologically suitable or pharmaceutically acceptable carrier or diluent. The carrier may be any physiologically acceptable buffer as is know in the art and includes but is not limited to phosphate buffered saline (PBS). Suitable methods of administration include but are not limited to: orally, parenterally, by injections or the like. Pharmaceutically effective concentrations and dosages of compositions comprising at least one histamine derivative will vary widely, depending upon the purpose, host and particular derivative employed. Concentrations may vary from less that 10-1M, and preferably less than or equal to 10-3M. Suitable single pharmaceutically effective dosages of such compositions range from about 0.5 mg/kg body weight to about 100 mg/kg. A preferred range is from about 1 mg/kg to 50 mg/kg. Suitable pharmaceutically effective daily total dosages range from about 1 mg/kg to 100 mg/kg.

The invention is further illustrated by the following non-limiting examples.

EXAMPLE 1

The following experiment shows the inhibition of the production of IgG antibodies in mice as well as the inhibition of the production of the IgG antibody subclasses IgG1, IgG2a, IgG2b (which comprise at least a portion of the total IgG response), as a result of administering to the mice compound 3 and challenging the mice with a T cell mediated antigen, horse myoglobin (h-Mb), which elicits an IgG antibody response.

Anti-Horse Myoglobin ELISA

ELISA plates were coated with 10 ug/ml commercially available horse myoglobin (h-Mb) in PBS 50 ul/well overnight at 4 deg C. The plates were washed with PBS once. The plates were then coated with 50 ul BBA (1 mg/ml) and washed with PBS once. The plates were then coated with test serum diluted in PBS-Tween, 50 ul/well and incubated at 4 deg C. overnight. The plates were then washed with PBS-Tween three times. Anti-IgG (1:2000) was added and diluted with PBS-Tween. For the IgG antibody subclasses, anti-IgG1, anti-IgG2a, anti-IgG2b was diluted and added to selected wells. Incubation was at 4 deg C. for two hours. Washing was with PBS-Tween 2 times with 5 minutes between each wash. A 1 mg/ml OPD in citrate buffer solution pH5 was prepared and 10 ul of H2O2/10 ml was added to the buffer solution. 50 ul of buffer was added to each well and the plates were placed in the dark for about 10 minutes. The reaction was stopped with 50 ul of 5N H2SO4 in each well. The plates were then read on an Elisa reader.

Immunization

The following immunization protocol was repeated several times. The results have been collected in FIGS. 1a–d.

This experiment was done using two groups of 2-6 DBA/2 mice (average weight 22 grams). One group of mice were given one treatment of compound 3 intravenously one day before antigen treatment (day-1) and two days following antigen treatment (day+2). The dose of compound 3 was approximately 36 mg/kg in 100 ul of PBS. The other group of mice was given a saline control in 100 ul PBS. On day 0 the two groups of mice were injected with 100 ug h-Mb in 100 ul CFA intravenously (i.v.). The mice were then boosted fourteen days later with 100 ug of h-Mb in 100 ul IFA. The mice were bled 30 days later.

TABLE 2

| Experimental Protocol | | | |
|---|---|---|---|
| Group 1 | 5 mice | Day 0, Day 14 | 100 ug h-Mb |
| | | Day − 1 & Day + 2 | 36 mg/kg compound 3 |
| Group 2 | 5 mice | Day 0, Day 14 | 100 ug h-Mb |
| | | Day − 1 & Day + 2 | PBS Control |

All sera was tested on the above described Elisa for IgG and IgG subclass antibody response to h-Mb. As shown in FIGS. 1*a–d*, mice immunized with compound 3 had a much lower total IgG response to h-Mb compared to the saline control mice here there was a significant IgG response. Furthermore, the mice immunized with compound 3 showed a lower IgG1, IgG2a and IgG2b response than did the saline control mice in all of those same IgG subclasses.

Figures 3A, 3B, 3C, 3D:
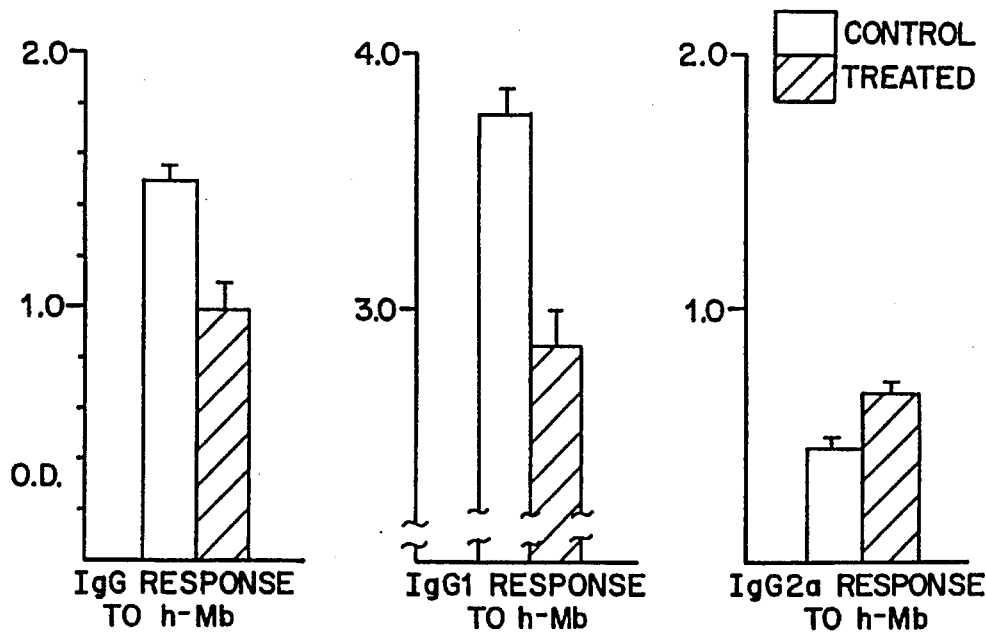

FIG. 3(*a–d*) shows results of a comparable experiment carried out using Compound 1. In this experiment, mice immunized with compound 1 show a lower IgG, IgG1 and IgG2a response than did the saline control mice.

EXAMPLE 2

The following experiment shows T cell proliferation in mice in response to treatment with compound 3 and challenge with commercially available sperm whale myoglobin (SpWMb) antigen. In this model, the response to SpWMb is mediated through CD4+ T Cells.

T Cell Proliferation Study

Two groups of DBA/2 mice were tested. One group of four mice was a control. The other group of four mice were treated with compound 3. Both groups of mice were immunized using approximately 100 ug per mouse of SpW-Mb plus CFA intravenously on day 0. On day-1 and day+2, one group of mice was given approximately 32 mg/kg compound 3 in 100 ul PBS i.v.

On day 8, the mice were killed and the draining lymph nodes were removed and a single cell suspension was made. The cells were then plated out in a 96 well U-bottom plate at a concentration of 4×106 cell/ml in media containing 1% mouse serum. The cells were then challenged in vitro with antigen diluted at 1, 5, and 25 uM in media without serum. The plates were then placed in the incubator at 37 deg C. On day 4 the wells were pulsed with tritiated thymidine and on day 5 the plates were harvested. The results are shown in FIG. 2.

What is claimed is:

1. A compound of the formula:

$$His—NH—(CH_2)_nCONH—phi—CF_3$$

wherein n=2–10 and phi-$CF_3$ is para-trifluromethylphenyl, and wherein said compound has H2 receptor activity but not H1 receptor activity.

2. The compound of claim 1 wherein n=3–6.

3. A compound of the formula:

$$His—NH—(CH_2)_nCONH—phi—CF_3$$

wherein n=2–10 and phi-$CF_3$ is para-trifluromethylphenyl, and wherein said compound has Hx receptor activity.

4. The compound of claim 3 wherein n=3–6.

5. A compound of the formula:

$$His—NH—(CH_2)_5CONH—phi—CF_3$$

wherein phi-$CF_3$ is para-trifluromethylphenyl.

6. A therapeutic composition comprising a histamine derivative having the formula:

$$His—NH—(CH_2)_nCONH—phi—CF_3$$

wherein n=2–10 and phi—$CF_3$ is para-trifluromethylphenyl, and a pharmaceutically acceptable carrier or diluent.

7. The composition of claim 6 wherein n=3–6.

8. The composition of 7 wherein the said histamine derivative has the formula:

$$His—NH—(CH_2)_5CONH—phi—CF_3$$

wherein phi—$CF_3$ is para-trifluromethylphenyl.

9. A composition comprising His—NH—$(CH_2)_5$CONH—phi—$CF_3$ and at least one compound selected from a group consisting of $$His—NH—CHCH_3—(CH_2)_3CONH—phi—CF_3$$

and $$His—NH—CHCH_3—(CH_2)_4CONH—phi—CF_3$$

wherein phi—$CF_3$ is para-trifluromethylphenyl.

* * * * *